United States Patent
McDonald et al.

(10) Patent No.: US 6,509,444 B1
(45) Date of Patent: Jan. 21, 2003

(54) SERUM AMYLOID A ISOFORM FROM COLOSTRUM

(75) Inventors: Thomas L. McDonald, Omaha, NE (US); Annika Weber, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/425,679

(22) Filed: Oct. 22, 1999

(51) Int. Cl.⁷ .............................................. C07K 14/00

(52) U.S. Cl. ...................... 530/344; 530/300; 530/328; 530/330

(58) Field of Search ................................. 530/415, 350, 530/380, 300, 328, 330, 344; 514/21, 12, 2

(56) References Cited

U.S. PATENT DOCUMENTS

| | | |
|---|---|---|
| 4,377,569 A | 3/1983 | Plymate |
| 4,425,330 A | 1/1984 | Norcross et al. |
| 5,227,301 A | 7/1993 | Turner et al. |
| 5,536,640 A | 7/1996 | Sipe et al. |
| 5,585,098 A | 12/1996 | Coleman |
| 5,700,465 A | 12/1997 | Tao et al. |

FOREIGN PATENT DOCUMENTS

| | | |
|---|---|---|
| EP | 0872 558 PO | 10/1998 |
| WO | WO 01 14580 CT | 3/2001 |

OTHER PUBLICATIONS

Syversen et al., "The primary structure of serum amyloid A protein in the sheep, comparison with serum amyloid A in other species," Scand. J. Immuno., vol. 39, pp. 88–94, 1994.*

Benson et al., "A unique insertion in the primary structure of bovine amyloid AA protein", J. Lab Clin Med, vol. 113, pp. 67–72, 1989.*

Bauman, H., et al., "The acucute phase response", IT Review, 1994 Elsevier Science Ltd, 0167–5699/94.

Hulten, C., et al., "The acute phase serum amyloid A protein (SAA) in the horse: isolation and characterization of three isoforms", Veterinary Immunology and Immunopathology 57(1997) 215–227.

Jensen, L., et al., "Regulation of serum amyloid A protein expression during the acute–phase response", Biochem J. (1998) 334489–503.

Kho, Y.J. et al., GenBank Submission AAF77630, serum amyloid A protein, [Bos taurus].

Liang, Jun–shan, et al., "Amino terminao region of acute phase, but not constitutive, serum amyloid A (apoSAA) specifically binds and transports cholesterol into aortic smooth muscle and HepG2 cells", Journal of Lipid Research (1996) 37:2109–2116.

Liepnieks, J., et al., "The primary structure of serum amyloid A protein in the rabbit: Comparison with serum amyloid A proteins in other species", J Lab Clin Med (1991) 118(6):570–576.

McDonald, T., et al., "A monoclonal antibody sandwich immunoassay for serum amyloid A (SAA) protein", J of Immunological Methods, 144 (1991) 149–155.

Malle, E., "Human serium amyloid A (SAA) protein: a prominent acute–phase reactant for clinical practice", European Journal of Clinical Investigation (1996) 26:427–435.

Migita, K., et al., "Serum Amyloid A Protein Induces Production of Matrix Metalloproteinases by Human Synovial Fibroblasts", Laboratory Investigation, 78(5):535–539 (1998).

Mitchell, T., et al., "The acute phase reactant serum amyloid A (SAA3) is a novel substrate for degradation by the metalloptoteinase collagenase and stromelysin", Biochem et Biophysica Acta. 1156 (1993) 245–254.

Patel, H., "Human Serium Amyloid A has Cytokine–Like Properties", Scand. J. Immunol., 1998, 48:410–418.

Peristeris, P., "Effects of serum amyloid A protein on lymphocytes, HeLa, and MRC5 cells in culture", Biochem. Cell Biol., (1989) 67:365–370.

Smith, J., et al., "Comparison of Serum Amyloid A and C–Reactive Protein as Indicators of Lung Inflammation in Corticosteroid Treated and Non–Corticosteroid Treated Cystic Fibrosis Patients", Journal of Clinical Laboratory Analysis 6:219–224 (1992).

Smith, J., et al., "Use of Ethanol–Eluted Hydrophobic Interaction Chromatography in the Purification of Serum Amyloid A", Protein Expression and Purification 2:158–161 (1991).

Smith, J., et al., "Production of serum amyloid A and C–reactive protein by HepG2 cells stimulated with combinations of cytokines or monocyte conditioned media: the effects of prednisolone", Clin. exp. Immunol. (1992) 783.

Steel, D., et al., "Expression and Regulation of Constitutive and Acute Phase Serum Amyloid A mRNAs in Hepatic and Non–Hepatic Cell Lines", 1996, Blackwell Science Ltd., Scandinavian Journal of Immunology, 44:493–500.

Steel, D., et al., "The major acute phase reactants: C–reactive protein, serum amyloid P component and serum and amyloid A protein", Review, 1994 Elsevier Science Ltd, 0167–5699/94.

(List continued on next page.)

*Primary Examiner*—Karen Cochrane Carlson
(74) *Attorney, Agent, or Firm*—McKee, Voorhees & Sease, P.L.C.

(57) ABSTRACT

A novel Serum Amyloid A (SAA), isolated and purified from mammalian colostrum, is disclosed. The SAA has been isolated from colostrum of several mammalian species, including horse, cow and sheep. Nucleic acid molecules encoding the colostrum SAA, and antibodies immunologically specific for the colostrum SAA, are also disclosed.

17 Claims, 1 Drawing Sheet

OTHER PUBLICATIONS

Thompson, D., et al., "The value of acute phase protein measurements in clinical practice", Ann Clin Biochem 1992, 29:123–131.

Uhlar, C., "Evolution of the Serum Amyloid A (SAA) Protein Superfamily", Genomics 19:228–235 (1994).

Urieli–Shoval, S., et al., "Widespread Expression of Serum Amyloid A in Histologically Normal Human Tisues: Predominant Localization to the Epithelium", The Journal of Histochemistry & Cytochemistry 46(12):1377–1384 (1998).

Zimlichman, S., "Serum amyloid A, an acute phase protein, inhibits platelet activation", Serum amyloid A and platelet activation, 116(2):180–186.

Mitchell, T.I. et al., "Serum Amyloid A (SAA3) Produced by Rabbit Synovial Fibroblasts Treated with Phorbol Esters or Interleukin 1 induces Synthesis of Collagenase and is Neutralized with Specific Antiserum", *J. Clinical Investigation* 87(4):1177–1185 (1991).

Rossevatn, K., et al., "The complete amino acidsequence of bovine serum amyloid protein A (SAA) and of subspecies of the tissue–deposited amyloid fibril protein A", *Scand. J. Immunol.* 35(2):217–24 (1992).

Sletten, K., "The Primary Structure of Equine Serum Amyloid A (SAA) Protein", *Scand. J. Immunol.* 30(1):117–122 (1989).

Kho Y.J., et al., "Cloning and characterization of involution–specific genes from the bovine mammary gland" Database EMBL accession No. AF160867 'Online! Jun. 30, 2000.

* cited by examiner

```
COW colSAA    (SEQ ID NO:1)          m wxtflkeagq gakdmwray
SHEEP colSAA  (SEQ ID NO:2)          w lltflkeag
HORSE colSAA  (SEQ ID NO:3)         re wftfl
HORSE colSAA  (SEQ ID NOs:4-8)      re lktflkeagq g
RABBIT SAA3      mklsigiifc flilgvnsre wltflkeagq gakdmwrays
HORSE SAA                                         llsflgeaar gtwdmirayn
MINK SAA1        mklftglifc slvlgvssq. wysfigeavq gawdmyrays
                 1

HORSE colSAA              eanyiga dkyfh    gny daaqrgpgga
RABBIT SAA3      dmkeanykns dkyfhargny daakrgpggv waaevisdar
HORSE SAA        dmreanyiga dkyfhargny daakrgpgga waakvisdar
MINK SAA1        dmreanykns dkyfhargny daaqrgpgga waakvisdar
                 41

HORSE colSAA              vtdlf k                    sgkdpnh
RABBIT SAA3      enyqklig.........rgae dskadqeanq wgrsgndpnh
HORSE SAA        enfqrftdrf sfggsgrgae dsradqaane wgrsgkdpnh
MINK SAA1        ersqrvtdlf kygdsghgve dskadqaane wgrsgkdpnh
                 81

HORSE colSAA     frphglpdky
RABBIT SAA3      frpkglpdky
HORSE SAA        frphglpdky
MINK SAA1        frpsglpdky
                 121
```

FIGURE 1

SEQUENCE LISTING

<160> NUMBER OF SEQ ID NOS: 13

<210> SEQ ID NO 1
<211> LENGTH: 20
<212> TYPE: PRT
<213> ORGANISM: Bos taurus
<220> FEATURE:
<221> NAME/KEY: MISC_FEATURE
<222> LOCATION: (3)..(3)
<223> OTHER INFORMATION: X can be any amino acid

<400> SEQUENCE: 1

Met Trp Xaa Thr Phe Leu Lys Glu Ala Gly Gln Gly Ala Lys Asp Met
1               5                   10                  15

Trp Arg Ala Tyr
            20

```
<210> SEQ ID NO 2
<211> LENGTH: 10
<212> TYPE: PRT
<213> ORGANISM: Ovis aries

<400> SEQUENCE: 2

Trp Leu Leu Thr Phe Leu Lys Glu Ala Gly
1               5                   10

<210> SEQ ID NO 3
<211> LENGTH: 13
<212> TYPE: PRT
<213> ORGANISM: Equus caballus

<400> SEQUENCE: 3

Arg Glu Leu Lys Thr Phe Leu Lys Glu Ala Gly Gln Gly
1               5                   10

<210> SEQ ID NO 4
<211> LENGTH: 7
<212> TYPE: PRT
<213> ORGANISM: Equus caballus

<400> SEQUENCE: 4

Arg Glu Trp Phe Thr Phe Leu
1               5

<210> SEQ ID NO 5
<211> LENGTH: 12
<212> TYPE: PRT
<213> ORGANISM: Equus caballus

<400> SEQUENCE: 5

Glu Ala Asn Tyr Ile Gly Ala Asp Lys Tyr Phe His
1               5                   10

<210> SEQ ID NO 6
<211> LENGTH: 13
<212> TYPE: PRT
<213> ORGANISM: Equus caballus

<400> SEQUENCE: 6

Gly Asn Tyr Asp Ala Ala Gln Arg Gly Pro Gly Gly Ala
1               5                   10

<210> SEQ ID NO 7
<211> LENGTH: 6
<212> TYPE: PRT
<213> ORGANISM: Equus caballus

<400> SEQUENCE: 7

Val Thr Asp Leu Phe Lys
1               5

<210> SEQ ID NO 8
<211> LENGTH: 17
<212> TYPE: PRT
<213> ORGANISM: Equus caballus

<400> SEQUENCE: 8

Ser Gly Lys Asp Pro Asn His Phe Arg Pro His Gly Leu Pro Asp Lys
1               5                   10                  15
Tyr
```

-continued

<210> SEQ ID NO 9
<211> LENGTH: 27
<212> TYPE: PRT
<213> ORGANISM: Oryctolagus cuniculus

<400> SEQUENCE: 9

Arg Glu Trp Leu Thr Phe Leu Lys Glu Ala Gly Gln Gly Ala Lys Asp
1               5                   10                  15

Met Trp Arg Ala Tyr Ser Asp Met Lys Glu Ala
            20                  25

<210> SEQ ID NO 10
<211> LENGTH: 110
<212> TYPE: PRT
<213> ORGANISM: Equus caballus

<400> SEQUENCE: 10

Leu Leu Ser Phe Leu Gly Glu Ala Ala Arg Gly Thr Trp Asp Met Ile
1               5                   10                  15

Arg Ala Tyr Asn Asp Met Arg Glu Ala Asn Tyr Ile Gly Ala Asp Lys
            20                  25                  30

Tyr Phe His Ala Arg Gly Asn Tyr Asp Ala Ala Lys Arg Gly Pro Gly
        35                  40                  45

Gly Ala Trp Ala Ala Lys Val Ile Ser Asp Ala Arg Glu Asn Phe Gln
    50                  55                  60

Arg Phe Thr Asp Arg Phe Ser Phe Gly Ser Gly Arg Gly Ala Glu
65                  70                  75                  80

Asp Ser Arg Ala Asp Gln Ala Ala Asn Glu Trp Gly Arg Ser Gly Lys
                85                  90                  95

Asp Pro Asn His Phe Arg Pro His Gly Leu Pro Asp Lys Tyr
            100                 105                 110

<210> SEQ ID NO 11
<211> LENGTH: 129
<212> TYPE: PRT
<213> ORGANISM: Mustela vison

<400> SEQUENCE: 11

Met Lys Leu Phe Thr Gly Leu Ile Phe Cys Ser Leu Val Leu Gly Val
1               5                   10                  15

Ser Ser Gln Trp Tyr Ser Phe Ile Gly Glu Ala Val Gln Gly Ala Trp
            20                  25                  30

Asp Met Tyr Arg Ala Tyr Ser Asp Met Arg Glu Ala Asn Tyr Lys Asn
        35                  40                  45

Ser Asp Lys Tyr Phe His Ala Arg Gly Asn Tyr Asp Ala Ala Gln Arg
    50                  55                  60

Gly Pro Gly Gly Ala Trp Ala Ala Lys Val Ile Ser Asp Ala Arg Glu
65                  70                  75                  80

Arg Ser Gln Arg Val Thr Asp Leu Phe Lys Tyr Gly Asp Ser Gly His
                85                  90                  95

Gly Val Glu Asp Ser Lys Ala Asp Gln Ala Ala Asn Glu Trp Gly Arg
            100                 105                 110

Ser Gly Lys Asp Pro Asn His Phe Arg Pro Ser Gly Leu Pro Asp Lys
        115                 120                 125

Tyr

```
<210> SEQ ID NO 12
<211> LENGTH: 7
<212> TYPE: PRT
<213> ORGANISM: artificial sequence
<220> FEATURE:
<223> OTHER INFORMATION: SAA consensus sequence Bos taurus
<220> FEATURE:
<221> NAME/KEY: MISC_FEATURE
<222> LOCATION: (1)..(3)
<223> OTHER INFORMATION: X can be any amino acid

<400> SEQUENCE: 12

Xaa Xaa Xaa Thr Phe Leu Lys
1               5

<210> SEQ ID NO 13
<211> LENGTH: 4
<212> TYPE: PRT
<213> ORGANISM: artificial sequence
<220> FEATURE:
<223> OTHER INFORMATION: Bos taurus consensus sequence

<400> SEQUENCE: 13

Thr Phe Leu Lys
1
```

SERUM AMYLOID A ISOFORM FROM COLOSTRUM

FIELD OF THE INVENTION

The present invention relates to the field of immunology and mammalian immune systems. In particular, the invention provides novel isoforms of serum amyloid A, which are found in colostrum.

BACKGROUND OF THE INVENTION

Several scientific or patent publications are referenced in this patent application to describe the state of the art to which the invention pertains. Each of these publications is incorporated by reference herein, in its entirety.

Mammals respond to tissue injury, trauma or infection by executing a complex series of biological reactions in an effort to prevent further tissue damage, to initiate repair of damaged tissue, and to isolate and destroy infective organisms. This process is referred to as the inflammatory response, the early and intermediate stages of which are referred to as the acute phase response.

The acute phase response involves a wide variety of mediators, including cytokines, interleukins and tumor necrosis factor. It also involves a radical alteration in the biosynthetic profile of the liver. Under normal circumstances, the liver synthesizes a range of plasma proteins at steady state concentrations. Some of these proteins, the "acute phase" proteins are induced in the inflammatory response to a level many times greater than levels found under normal conditions. Acute phase proteins are reviewed by Steel & Whitehead (Immunology Today 15: 81–87, 1994).

One of the massively induced acute phase proteins is Serum Amyloid A (SAA). SAA actually comprises a family of polymorphic proteins encoded by many genes in a number of mammalian species. SAAs are small apolipoproteins that accumulate and associate rapidly with high-density lipoprotein 3 (HDL3) during the acute phase of the inflammatory response. Most SAA isoforms are induced in response to inflammation; however, certain SAAs (e.g., human SAA4) appear to be constitutively expressed or minimally induced in the inflammatory response.

The liver has been considered the primary site of SAA production. However, SAA production outside the liver has been found, on a limited basis. For instance, expression of SAA mRNA has been reported in human atherosclerotic lesions and in human cultured smooth muscle cells and monocyte/macrophage cell lines (Meek et al., 1994; Urieli-Shoval et al., 1994; Yamada et al., 1996), and a unique isoform of SAA (SAA3) is produced by rabbit synovial fibroblasts (Mitchell et al., J. Clin. Invest. 87: 1177–1185, 1991). More recently, it was discovered that SAA mRNA is widely expressed in many histologically normal epithelial tissues, including tissues of stomach, intestine, tonsil, breast, prostate, thyroid, lung, pancreas, kidney, skin and brain neurons (Urieli-Shoval et al., J. Histochem. Cytochem. 46: 1377–1384, 1998). The role of SAA in such tissues has not been elucidated, nor has it been determined if the SAAs present in those tissues are the same isoforms as those found in serum, or if they represent additional isoforms of SAA.

SUMMARY OF THE INVENTION

According to one aspect of the invention, a Serum Amyloid A (SAA) protein is provided, which is isolated and purified from mammalian colostrum. In one embodiment, the SAA is isolated and purified from horse colostrum. Preferably, the horse colostrum SAA comprises SEQ ID NO:3 or SEQ ID NO:4 and one or more of a sequence selected from the group consisting of SEQ ID NO:5, SEQ ID NO:6, SEQ ID NO:7 and SEQ ID NO:8.

In another embodiment, the SAA is isolated and purified from cow colostrum, and preferably comprises an N-terminal amino acid sequence which is SEQ ID NO:1. Alternatively, the SAA is isolated and purified from sheep colostrum and preferably comprises an N-terminal amino acid sequence which is SEQ ID NO:2.

According to another aspect of the invention, an isolated nucleic acid molecule that encodes a mammalian colostrum SAA is provided. The nucleic acid molecule may be a gene, cDNA or RNA and may be single-stranded or double stranded. In a preferred embodiment, the nucleic acid molecule comprises a sequence that encodes one or more of SEQ ID NO: 1–8.

According to another aspect of the invention, a population of synthetic oligonucleotides is provided, which includes sequences obtained by back-translating one or more of amino acid SEQ ID NOS: 1–8. One or more members of this population of oligonucleotides specifically hybridizes to a gene or cDNA that encodes a colostrum SAA.

According to another aspect of the invention, antibodies immunologically specific for one or more epitopes of colostrum SAA. Preferably, the antibodies are immunologically specific for at least one epitope of the colostrum SAA that distinguishes colostrum SAA from serum SAA.

According to another aspect of the invention, a process is provided for obtaining SAA from a mammal. The process comprises the steps of: (1) providing a sample of colostrum from the mammal, and (2) separating SAA contained in the sample from other materials contained in the sample, thereby obtaining the SAA from the mammal. SAA produced by this process is also provided.

Other features and advantages of the present invention will be better understood by reference to the drawings, detailed descriptions and examples that follow.

BRIEF DESCRIPTION OF THE DRAWING

FIG. 1. N-terminal amino acid sequence alignment of tryptic fragments of cow (SEQ ID NO:1), sheep (SEQ ID NO:2) and horse (SEQ ID NO:3) colostrum SAA, tryptic digest fragments of horse colostrum SAA (SEQ ID NOS: 4–8), rabbit synovial fibroblast SAA3 (SEQ ID NO:9; horse serum SAA, (SEQ ID NO:10); and mink serum SAA1, (SEQ ID NO:11).

DETAILED DESCRIPTION OF THE INVENTION

I. Definitions

Various terms relating to the compositions and methods of the present invention are used hereinabove and also throughout the specification and claims.

With respect to proteins or peptides, the term "isolated protein (or peptide)" or "isolated and purified protein (or peptide)" is sometimes used herein. This term may refer to a protein that has been sufficiently separated from other proteins with which it would naturally be associated, so as to exist in "substantially pure" form. Alternatively, this term may refer to a protein produced by expression of an isolated nucleic acid molecule.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

Nucleic acid sequences and amino acid sequences can be compared using computer programs that align the similar sequences of the nucleic or amino acids thus define the differences. The BLAST programs (NCBI) and parameters used therein are used by many practitioners to align amino acid sequence fragments. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

The term "substantially the same" refers to nucleic acid or amino acid sequences having sequence variation that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to antibodies, the term "immunologically specific" refers to antibodies that bind to one or more epitopes of a protein of interest, but which do not substantially recognize and bind other molecules in a sample containing a mixed population of antigenic biological molecules.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (51 direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In procaryotes, yeast, and mammalian cells for example, the transforming DNA may be maintained on an episomal element such as a plasmid. With respect to eucaryotic cells, a stably transformed cell is one in which the transforming DNA has become integrated into a chromosome so that it is inherited by daughter cells through chromosome replication. This stability is demonstrated by the ability of the eucaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

II. Description

Serum amyloid A (SAA) is an acute phase protein which is produced in the liver and occurs at elevated levels in the serum of mammals as part of the inflammatory response related to tissue injury or infection. The inventors have discovered a unique form of SAA that occurs at highly elevated levels in colostrum. Elevated colostrum SAA in cows returns to background levels found in milk within four days after calving. It is believed to be produced locally (i.e., in mammary ductal epithelial cells), as it occurs independently of the blood concentration of acute SAA (in samples of colostrum, whey and serum taken from five test cows, serum SAA was found to be in the range of 15 µg/ml, while in colostrum, SAA was elevated to levels in the average range of 300 µg/ml).

SAA in colostrum may be fulfilling a variety of functions relating to the general role of colostrum in the development of neonatal immunity. For instance, colostrum SAA may act as vehicle for transport of lipids and immunoglobulins across the endothelial membranes of gut and/or vasculature in the newborn. It may be produced locally by the vascular endothelium after injury, and serve as a vehicle for transport of immunoglobulins into the intravascular space. In general, colostrum SAA is likely to have anti-microbial activity (either directly or indirectly) and to regulate the immune response in some manner. SAA also may be involved in tissue remodeling by inducing enzymes involved in tissue repair and degradation, and by regulating production of protective mucins in mucosal tissue.

An elevated level of SAA has been detected in the colostrum of cows, horses, sheep and pigs. It has been purified from cow, sheep and horse colostrum, using methods such as those described in Example 3. Purified colostrum SAA from these sources was subjected to N-terminal amino acid sequence analysis. These sequences are set forth below, compared with the corresponding sequence of SAA3 from rabbit synovial fibroblasts.

Colostrum:
Cow (SEQ ID NO:1): MWXTFLKEAGQGAKDM-WRAY
Sheep (SEQ ID NO:2): WLLTFLKEAG
Horse (SEQ ID NO:3): RELKTFLKEAGQG Synovial fibroblasts:
Rabbit SAA3
(Part if SEQ ID NO:9): REWLTFLKEAGQGAKDM-WRAYSDMKEA As can be seen, the colostrum-derived SAAs share a unique amino acid sequence in the amino-terminal end (TFLK). This sequence is not found in any of the serum-derived SAAs from any mammal, but does share homology with SAA3 produced by rabbit synovial fibroblasts. The human SAA pseudogene (not expressed in serum) also comprises a deduced amino acid sequence that contains the TFLK sequence motif.

Further analysis of tryptic digest fragments of horse colostrum SAA revealed, however, that colostrum SAA is indeed a unique SAA. Sequences of the tryptic fragments of horse colostrum SAA are set forth below (SEQ ID NO: 4 is an alternate of SEQ ID NO:3).

SEQ ID NO:4 REWFTFL
SEQ ID NO:5: EANYIGADKYFH
SEQ ID NO:6: GNYDAAQRGPGGA
SEQ ID NO:7: VTDLFK
SEQ ID NO:8: SGKDPNHFRPHGLPDKY

In FIG. 1, the five horse colostrum SAA tryptic fragment sequences(SEQ ID NOS: 3–8) and the N-terminal sequences from cow and sheep and horse colostrum SAA (SEQ ID NOS: 1–3) are shown in alignment with the complete amino acid sequences of synovial fibroblast SAA3 from rabbit (SEQ ID NO:9), horse serum SAA (SEQ ID NO:10) and serum SAA1 from mink (SEQ ID NO:11). As can be seen from the alignment, horse colostrum SAA shares regions of similarity with each of rabbit synovial fibroblast SAA3, horse serum SAA and mink serum SAA1, yet is distinct from each of these proteins.

Thus, the present invention provides novel SAA isoforms isolated from colostrum. Although the horse, cow and sheep colostrum SAAs are exemplified herein, the present invention includes colostrum SAA isoforms from any mammalian species, inasmuch as the present inventors have identified colostrum SAAs from several mammalian species. Furthermore, as described in greater detail below, nucleic acid molecules encoding colostrum SAAs are also contemplated as being part of the present invention, as are antibodies immunologically specific for these novel SAA isoforms.

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning,* Cold Spring Harbor Laboratory (1989) (hereinafter "Sambrook et al.") or Ausubel et al. (eds) *Current Protocols in Molecular Biology,* John Wiley & Sons (1999) (hereinafter "Ausubel et al.") are used.

A. Preparation of Colostrum SAA, Antibodies Specific for Colostrum SAA and Nucleic Acid Molecules Encoding Colostrum SAA 2. Proteins and Antibodies Colostrum SAA may be prepared in a variety of ways, according to a variety of methods that have been developed for purifying SAA from serum. One such method is set forth in Example 3. Variations in hydrophobic chromatography matrix systems and eluants also may be employed, such as those described by Smith et al. (Protein Expression & Purification 2: 158–161, 1991).

Alternatively, the availability of amino acid sequence information, such as SEQ ID NOS: 1–8, enables the isolation of nucleic acid molecules encoding colostrum SAA. This may be accomplished using anti-colostrum SAA antibodies to screen a cDNA expression library from a selected species, according to methods well known in the art. Alternatively, a series of degenerate oligonucleotide probes encoding parts or all of SEQ ID NOS: 1–8 may be used to screen cDNA or genomic libraries, as described in greater detail below.

Once obtained, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. The pCITE in vitro translation system (Novagen) also may be utilized.

According to a preferred embodiment, larger quantities of the proteins may be produced by expression in a suitable procaryotic or eucaryotic system. For example, part or all of a colostrum SAA-encoding DNA molecule may be inserted into a vector adapted for expression in a bacterial cell (such as *E. coli*) or a yeast cell (such as *Saccharomyces cerevisiae*), or a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

Colostrum SAA produced by gene expression in a recombinant procaryotic or eucaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The present invention also provides antibodies capable of binding to colostrum SAA from one or more selected species. Polyclonal or monoclonal antibodies directed toward part or all of a selected colostrum SAA may be prepared according to standard methods. Monoclonal antibodies may be prepared according to general methods of Köhler and Milstein, following standard protocols. In a preferred embodiment, antibodies are prepared, which react immunospecifically with selected epitopes of colostrum SAA that distinguish it from other SAAs.

2. Nucleic Acid Molecules

Once sequence information is obtained, nucleic acid molecules encoding colostrum SAA may be prepared by two general methods: (1) they may be synthesized from appropriate nucleotide triphosphates, or (2) they may be isolated from biological sources. Both methods utilize protocols well known in the art.

The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Nucleic acid molecules encoding colostrum SAA also may be isolated from mammalian species of interest using methods well known in the art. Nucleic acid molecules from a selected species may be isolated by screening cDNA or genomic libraries with oligonucleotides designed to match a nucleic acid sequence specific to a colostrum SAA-encoding gene. If the gene from a species is desired, the genomic library is screened. Alternatively, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al., *Molecular Cloning,* 1989, Cold Spring Harbor Press, Cold Spring Harbor N.Y.).

Alternatively, PCR (polymerase chain reaction) primers may be designed by the above method to encode a portion of colostrum SAA protein, and these primers used to amplify nucleic acids from isolated cDNA or genomic DNA. In a preferred embodiment, the oligonucleotides used to isolate colostrum SAA-encoding nucleic acids are designed to encode sequences unique to colostrum SAA, as opposed to serum SAA.

In accordance with the present invention, nucleic acids having the appropriate sequence homology with a colostrum SAA-encoding nucleic acid molecule may be identified by using hybridization and washing conditions of appropriate stringency. For example, hybridizations may be performed, according to the method of Sambrook et al. (1989, supra), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology (Sambrook et al., 1989, supra):

$$T_m = 81.5° \text{ C.} + 16.6\text{Log}[Na+] + 0.41(\%G+C) - 0.63(\%\text{formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. In a preferred embodiment, the hybridization is at 37° C. and the final wash is at 42° C., in a more preferred embodiment the hybridization is at 42° and the final wash is at 50°, and in a most preferred embodiment the hybridization is at 42° C. and final wash is at 65° C., with the above hybridization and wash solutions.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and wash in 0.1×SSC and 0.5% SDS at 65° C. for 15 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable E. coli host cell.

Colostrum SAA-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting colostrum SAA-encoding genes or mRNA in test samples, e.g. by PCR amplification.

B. Uses of Colostrum SAA Protein, Antibodies and Nucleic Acids

1. Proteins and Antibodies

Purified colostrum SAA, or fragments thereof, may be used to produce polyclonal or monoclonal antibodies which may serve as sensitive detection reagents for the presence and accumulation of the proteins in cultured cells or tissues and in intact organisms. Recombinant techniques enable expression of fusion proteins containing part or all of a selected colostrum SAA. The full length protein or fragments of the protein may be used to advantage to generate an array of monoclonal or polyclonal antibodies specific for various epitopes of the protein, thereby providing even greater sensitivity for detection of the protein. In a preferred embodiment, fragments of colostrum SAA that distinguish colostrum SAA from serum SAAs are utilized for generating epitope-specific antibodies.

Polyclonal or monoclonal antibodies immunologically specific for colostrum SAA may be used in a variety of assays designed to detect and quantitate the proteins. Such assays include, but are not limited to, (1) immunoprecipitation followed by protein quantification; (2) immunoblot analysis (e.g., dot blot, Western blot) (3) radioimmune assays, (4) nephlometry, turbidometric or immunochromatographic (lateral flow) assays, and (5) enzyme-coupled assays, including ELISA and a variety of qualitative rapid tests (e.g., dip-stick and similar tests).

Polyclonal or monoclonal antibodies that immunospecifically interact with colostrum SAA can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

2. Nucleic Acids

Colostrum SAA-encoding nucleic acids may be used for a variety of purposes in accordance with the present invention. The DNA, RNA, or fragments thereof may be used as probes to detect the presence of and/or expression of the genes. Methods in which colostrum SAA-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The exemplified colostrum SAA-encoding nucleic acids of the invention (e.g., cow, sheep, horse) may also be utilized as probes to identify related genes from other species, including humans. As is well known in the art and described above, hybridization stringencies may be adjusted to allow hybridization of nucleic acid probes with complementary sequences of varying degrees of homology.

In addition to the aforementioned uses of colostrum SAA-encoding nucleic acids, they are expected to be of utility in the creation of transgenic cells, tissues and organisms.

3. Assays Based on the Discovery Of SAA in Colostrum

The discovery of a specific, constitutively expressed form of SAA in colostrum enables a new way of detecting the presence of colostrum in a sample containing a mixture of biological fluids (e.g., colostrum and milk). For instance, since SAA is elevated in colostrum and not in milk from normal breast tissue, the measurement of SAA in a milk sample can be used to differentiate colostrum from milk. Accordingly, in instances where it is undesirable to have milk that contains colostrum (some countries have laws to this effect), an immunological or hybridization assay, as described above, may be used to detect colostrum-tainted milk.

Colostrum SAA also may be used for a variety of other purposes. These include, but are not limited to its use as (1) a carrier for delivery of molecules across the gut or vasculature, (2) a nutritional supplement for development of the gut mucosa in newborns, and (3) as a regulator of immune responses (via injection or oral administration).

The following examples are provided to describe the invention in greater detail. They are intended to illustrate, not to limit, the invention.

EXAMPLE 1

Comparative Analysis of SAA in Serum, Colostrum and Whey

The purpose of this study was to determine if SAA levels in colostrum and whey corresponded to serum SAA levels in mastitis symptomless and symptomatic cows.

Colostrum, whey and serum samples were obtained from a challenge model study in which cattle were vaccinated against a gram positive organism. Two sets of samples were utilized: one set (4 cows) from vaccinated animals that displayed clinical symptoms of mastitis, and the other set (5 cows) from vaccinated animals showing no clinical symptoms. Sample designations are shown below:

| Vaccinates - Non Clinical (NC) | Vaccinates - Clinical (C) |
|---|---|
| NC Cow A | C Cow A |
| NC Cow B | C Cow B |
| NC Cow C | C Cow C |
| NC Cow D | C Cow D |
| NC Cow E | |

Whey/colostrum samples were obtained from the quarter displaying the clinical symptoms.

ELISA assays were conducted according to standard protocols, e.g., as described by McDonald et al. (J. Immunol. Meth. 144: 149–155, 1991), using rat anti-SAA (human) monoclonal antibodies that cross react with bovine SAA isoforms.

Results are shown in Table 1:

TABLE 1

Comparison of Bovine Mastitis Sera, Whey and Colostrum SAA values

| | Nonclinical Samples: | | | Clinical Samples: | |
|---|---|---|---|---|---|
| Sample | Sera ug/ml | Whey/ Colost. ug/ml | Sample | Sera ug/ml | Whey Colost. ug/ml |
| NCA Day 0 | 3.9 | 2.3 | CA Day 0 | 1.3 | 0.8 |
| NCA Day 14 | 1.4 | | CA Day 14 | 1.9 | |
| NCA Day 28 | 1.0 | | CA Day 28 | 1.1 | |
| NCA Day 42 | 1.1 | | CA Day 42 | 0.8 | |
| NCA calving | 13.6 | 117.8 | CA Calving | 3.6 | 1108.0 |
| NCA-C + 14 | 73.0 | 56.5 | CA C + 14 | 12.3 | 0.8 |
| NCA-C + 28 | 11.8 | 3.4 | CA C + 28 | 152.6 | 55.0 |
| NCB Day 0 | 2.6 | 2.3 | CB Day 0 | 2.7 | 1.8 |
| NCB Day 14 | 1.4 | | CB Day 14 | 21.4 | |
| NCB Day 28 | 1.2 | | CB Day 28 | 3.1 | |
| NCB Day 42 | 0.8 | | CB Day 42 | 1.0 | |
| NCB calving | 4.6 | 346.2 | CB Calving | 17.2 | 291.0 |
| NCB-C + 14 | 1.2 | 4.0 | CB C + 14 | 26.7 | 1.7 |
| NCB-C + 28 | 0.8 | 7.3 | CB C + 28 | 7.2 | 3.7 |
| NCC Day 0 | 3.1 | 1.8 | CC Day 0 | 1.9 | 1.9 |
| NCC Day 14 | 1.8 | | CC Day 14 | 2.0 | |
| NCC Day 28 | 1.4 | | CC Day 28 | 2.0 | |
| NCC Day 42 | 0.9 | | CC Day 42 | 0.9 | |
| NCC Calving | 24.5 | 15.8 | CC Calving | 18.0 | 5.8 |
| NCC C + 14 | 6.9 | 1.4 | CC C + 14 | 167.9 | 30.0 |
| NCC C + 28 | 6.8 | 9.1 | CC C + 28 | 1.3 | 8.4 |
| NCD Day 0 | 3.2 | 1.7 | CD Day 0 | 2.7 | 3.4 |
| NCD Day 14 | 0.9 | | CD Day 14 | 1.6 | |
| NCD Day 28 | 2.4 | | CD Day 28 | 1.8 | |
| NCD Day 42 | 0.8 | | CD Day 42 | 1.6 | |
| NCD Calving | 13.8 | 484.4 | CD Calving | 14.6 | 77.5 |
| NCD C + 14 | 1.3 | 1.6 | CD C + 14 | 1629.0 | 999.5 |
| NCD C + 28 | 1.2 | 5.0 | CD C + 28 | 33.1 | 2.5 |
| NCE Day 0 | 2.6 | 8.0 | | | |
| NCE Day 14 | 1.6 | | | | |
| NCE Day 28 | 1.9 | | | | |
| NCE Day 42 | 1.0 | | | | |
| NCE Calving | 33.2 | 89.1 | | | |
| NCE C + 14 | 7.8 | 0.6 | | | |
| NCE C + 28 | 5.5 | 4.3 | | | |

As can be seen from the results set forth in Table 1, SAA was present in high levels in the colostrum of cows at calving in 80% of the animals tested. SAA was not present in whey samples fourteen days later. SAA levels in colostrum and whey were independent of the serum concentrations of SAA. Serum levels of SAA at calving of control cows were normal (15 $\mu$g/ml), whereas the average level in the colostrum at calving was about 300 $\mu$g/ml. In one cow, the colostrum SAA was as high as 1100 $\mu$g/ml. The mastitis challenged vaccinated cow CC displayed highly elevated serum levels of SAA, but SAA levels in the whey samples were almost normal. The vaccinated challenged cow CD displayed high levels of SAA in serum and in whey.

EXAMPLE 2

Evaluation of SAA in Colostrum and Subsequent Serial Samplings of Milk

The purpose of this study was to evaluate colostrum and subsequent serial milk samplings to determine SAA content. Samples were obtained from Holstein dairy cows at the University of Nebraska—Lincoln Dairy Research Facility. Samples of colostrum were taken at calving, and subsequent milk samples were taken twice weekly for three weeks. Samples from all four udder quadrants were pooled. Results are shown in Table 2.

TABLE 2

SAA Levels in Colostrum and Milk Samples

| Cow ID | Sample Day | SAA ug/ml |
|---|---|---|
| 83 colostrum | Calving | 184.8 |
| 83 milk | +4 | 0.2 |
| 83 milk | +7 | 0.0 |
| 83 milk | +11 | 0.0 |
| 83 milk | +14 | 0.0 |
| 83 milk | +18 | 0.0 |
| 83 milk | +21 | 0.0 |
| 908 colostrum | Calving | 135.6 |
| 908 milk | +4 | 2.6 |
| 908 milk | +7 | 9.1 |
| 908 milk | +11 | 8.2 |
| 908 milk | +14 | 2.0 |
| 908 milk | +18 | 2.1 |
| 908 milk | +21 | 3.6 |
| 961 colostrum | Calving | 364.6 |
| 961 milk | +4 | 0.3 |
| 961 milk | +7 | 0.5 |
| 961 milk | +11 | 0.0 |
| 961 milk | +14 | 0.0 |
| 961 milk | +18 | 0.0 |
| 961 milk | +21 | 0.0 |

The results show that SAA is present in colostrum of normal animals but not in normal milk samples after colostrum has cleared.

EXAMPLE 3

Purification of SAA from Colostrum

The procedure set forth below can be used for purification of SAA from serum, plasma, milk or colostrum from any animal species. The procedure comprises two basic steps: the SAA is purified to approximately 20% purity by hydrophobic chromatography, then further purified to approximately 95% purity by SDS-PAGE and electro-blotting.

Approximately 30 ml of octyl sepharose CL-4B (Pharmacia #17-0790-01) was prepared by washing it with approximately 10 volumes (300 ml) water to remove any traces of ethanol. This may be done by washing the gel in a sintered glass funnel (coarse, funnel volume 600 ml) or by adding the water to the gel in a beaker, and then allowing the gel to settle before pouring off the water and rewashing the gel.

The final washes (2×40 ml) of the gel were with a solution of 0.5 M ammonium sulfate.

After the ammonium sulfate was poured off, 20 ml colostrum with elevated levels of SAA (preferably>1 mg/ml) was added to the gel (in the beaker). Before colostrum was added to the gel, the colostrum was allowed to set at 4° C. to allow the lipid layer to separate from the aqueous layer, since the lipid portion seemed to interfere with the purification procedure. The suspension was swirled several times during the one hour incubation at room temperature so to allow the SAA to bind to the gel.

The gel was then poured into a 600 ml sintered glass funnel (coarse) and the non-bound fraction was collected. This non-bound fraction may be tested for SAA to determine the efficiency of binding.

The gel was washed with 5-X 50 ml 50 mM TRIS, 10 mM NaCl buffer pH 7.6. The final wash should be clear.

The column was further washed with 2×50 ml of 30% isopropanol in TRIS/NaCl. These washes were most thorough when a syringe with a 10 gauge needle was used to eject the isopropanol/buffer solution onto the gel. The gel was thoroughly mixed when this procedure was followed.

The SAA was eluted from the gel with a solution of 60% isopropanol in TRIS/NaCl. Generally this was done in four elutions of 10 ml each.

The eluates contained a variety of proteins, of which about 20% was SAA. In samples where the SAA was too dilute it was concentrated by evaporating the isopropanol in a centrifugal concentrator.

For further purification for sequencing or amino acid analysis the proteins in the eluates were separated by SDS-PAGE and transferred to IPVD membrane by electro-blotting. The band which is identified as SAA by SAA specific antibodies was then excised and used for sequencing.

The present invention is not limited to the embodiments described above, but is capable of modification within the scope of the appended claims.

---

We claim:

1. An isolated and purified Serum Amyloid A (SAA) protein present in mammalian colostrum, wherein said SAA protein comprises a sequence selected from the group consisting of SEQ ID NOS: 1–6 and SEQ ID NO: 8.

2. The SAA protein of claim 1, wherein SEQ ID No: 1 is isolated and purified from cow colostrum.

3. The SAA protein of claim 1, wherein SEQ ID NO: 2 is isolated and purified from sheep colostrum.

4. The SAA protein of claim 1, wherein SEQ ID NOS: 3, 4, 5, 6 and SEQ ID NO: 8 are isolated and purified from horse colostrum.

5. An isolated and purified serum amyloid A (SAA) protein wherein said protein is characterized by the following:

is present in mammalian colostrum;

and comprises the amino acid sequence set forth in SEQ ID NO: 1.

6. A purified and isolated serum amyloid A (SAA) protein wherein said protein is present in mammalian colostrum and comprises an amino acid SEQ ID NO:2.

7. A purified and isolated serum amyloid A (SAA) protein wherein said protein is present in mammalian colostrum and comprises an amino acid SEQ ID NO:3.

8. A purified and isolated serum amyloid A (SAA) protein wherein said protein is present in mammalian colostrum and comprises amino acid SEQ ID NOS:4, 5, 6 and 8.

9. An isolated and purified serum amyloid A (SAA) protein, said protein comprising an N-terminal amino acid sequence of Xaa Xaa Xaa Thr Phe Leu Lys (SEQ ID NO:12) where Xaa can be any amino acid.

10. A purified and isolated protein, said protein comprising: a Thr Phe Leu Lys motif (SEQ ID NO:13) in the N-terminal eight amino acids of said protein.

11. An isolated and purified serum amyloid A (SAA) protein wherein said protein is present in mammalian colostrum and comprises a Thr Phe Leu Lys motif (SEQ ID NO:13) in the N-terminal eight amino acids thereof.

12. A purified and isolated serum amyloid A protein, said protein being present in colostrum and comprises Thr Phe Leu Lys motif (SEQ ID NO:13) in the N-terminal eight amino acids of said protein and wherein said protein regulates mucin production.

13. A purified and isolated serum amyloid A (SAA) protein, said protein comprising one which reacts with an antibody having an epitope that interacts with a serum amyloid A protein that is a non-acute phase protein, is secreted by ductal epithelial cells and, is minimally induced in response to inflammation, is present in colostrum and has a Thr Phe Leu Lys motif (SEQ ID NO:13) in the N-terminal eight amino acids of said protein.

14. An isolated and purified protein characterized by the following:

a) a non-acute phase protein b) secreted by ductal epithelial cells c) minimally induced in response to inflammation d) present in colostrum; and e) a Thr Phe Leu Lys motif (SEQ ID NO:13) in the N-terminal eight amino acids of said protein.

15. The protein of claim 14 wherein said protein is a member of the SAA gene family.

16. A process for obtaining a serum amyloid A (SAA) protein from a mammal, comprising the steps of:

a) providing a sample of colostrum from the mammal; and b) separating SAA from other materials contained in the sample, thereby obtaining the SAA from the mammal.

17. The process of claim 16, wherein the mammal is selected from the group consisting of cows, horses, pigs, sheep and humans.

* * * * *